United States Patent [19]

Meisterling

[11] Patent Number: 4,760,740

[45] Date of Patent: Aug. 2, 1988

[54] VACUUM COUPLED TRANSDUCER

[75] Inventor: Jesse R. Meisterling, East Hampton, Conn.

[73] Assignee: Raymond Engineering Inc., Middletown, Conn.

[21] Appl. No.: 76,773

[22] Filed: Jul. 22, 1987

[51] Int. Cl.⁴ ............................................. G01N 29/00
[52] U.S. Cl. ........................................ 73/761; 269/21
[58] Field of Search ...................... 73/761, 866.5, 581; 248/205.5, 205.6, 205.7, 205.8; 269/21

[56] References Cited

U.S. PATENT DOCUMENTS 3,810,385 5/1974 McFaul et al. ................. 73/581 X
4,217,849 8/1980 Brown et al. ................... 73/761 X Primary Examiner—Jerry W. Myracle
Attorney, Agent, or Firm—Fishman, Dionne & Cantor

[57] ABSTRACT

A vacuum coupled ultrasonic transducer is presented for coupling a transducer to a bolt for ultrasonic measurement of bolt elongation. A central passageway extends through the transducer body, the piezoelectric crystal and a seal element. A vacuum line extends through the central passageway.

5 Claims, 2 Drawing Sheets

VACUUM COUPLED TRANSDUCER

BACKGROUND OF THE INVENTION

This invention relates to ultrasonic transducer apparatus used in the measuring of bolt elongation. More particularly, this invention relates to apparatus for vacuum coupling an ultrasonic transducer to a bolt for measurement of elongation of the bolt.

The technology, including apparatus and methods, of ultrasonically measuring the elongation of bolts to determine load or tightening of the bolt is well known. Apparatus and methods of varying degrees of sophistication are shown, for example in U.S. Pat. Nos. 3,759,090, 3,810,385, 3,969,810, 4,423,518 and 4,471,651 (that list of prior art patents being intended merely as a sampling and not intended to be a comprehensive listing of prior art patents in the field).

Regardless of the level of sophistication of the technology, it all uses an ultrasonic transducer in contact with the bolt whose elongation is to be ultrasonically measured. In response to electronic input pulses, the transducer sends an ultrasonic pulse along the length of the bolt, senses the echo from the end of the bolt, and delivers a measurement signal to the measuring and detecting circuitry of the apparatus.

A recognized problem area in the technology of ultrasonic measurement of bolt elongation is in maintaining firm and continuous contact between the transducer and the bolt being measured. Reliable measurements can not be obtained if firm and continuous contact is not maintained between the transducer and the head of the bolt. The prior art has typically used a couplant material such as oil or glycerine between the bolt and a means for holding the transducer in place while the ultrasonic measurement is made. The holding means have been mechanically or magnetically accomplished by threaded connections or angular magnets around the transducer. While the use of such holding techniques is generally effective, it has a number of drawbacks such as mechanical mounting which is difficult to accomplish, failure of magnetic means on nonmagnetic materials and attractions of magnetic debris on the transducer face.

SUMMARY OF THE INVENTION

The present invention eliminates or reduces the attachment problem of the prior art and can eliminate the need for a lubricant or other couplant. In accordance with the present invention, the transducer is vacuum coupled to the bolt by means of a vacuum line incorporated in the transducer. The surface of the transducer which contacts the bolt is provided with an ultrasonically compatible flexible material which conforms to the surface of the bolt head. The force produced by the vacuum at the transducer/bolt interface holds the transducer in firm and continuous contact with the bolt, and the flexible material conforms to the head of the bolt and forms an air tight seal.

The present invention eliminates the need for lubricant type couplants on flat surfaces and achieves an effective and reliable coupling between the ultrasonic transducer and the head of the bolt to be measured.

BRIEF DESCRIPTION OF THE DRAWINGS

Referring to the drawings, wherein like elements are numbered alike in the several FIGURES.

DESCRIPTION OF THE PREFERRED EMBODIMENT

Figure 1:
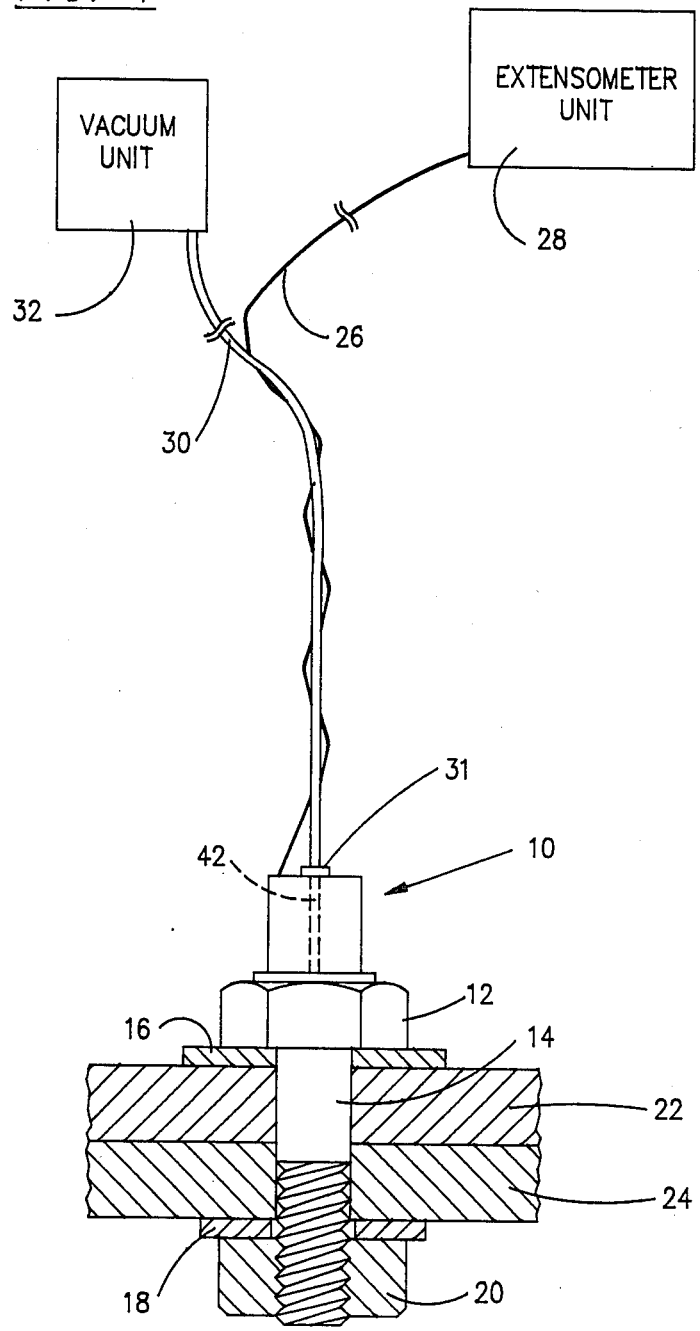
FIG. 1 is a general showing of an ultrasonic measuring system with a vacuum coupled transducer in accordance with the present invention.

Referring to FIG. 1, there is a generalized showing of the vacuum coupled transducer of this invention in a typical environment of a fastened joint. The ultrasonic transducer unit 10 is mounted on the head 12 of a bolt 14 whose elongation is to be measured. Transducer 10 may be any suitable ultrasonic transducer (modified in accordance with the present invention), such as shown, e.g., in U.S. Pat. Nos. 3,759,090, 3,810,385 and 3,969,810, all of which are incorporated herein by reference. The joint further includes washers 16 and 18, a nut 20 and two plates 22 and 24 which are being fastened together.

An electrical signal transmission line 26 extends between ultrasonic transducer unit 10 and an extensometer unit 28 which is the signal generating, receiving, amplifying and processing unit. Extensometer unit 28 generates the pulse which triggers the ultrasonic transducer 10 to produce an ultrasonic signal to traverse bolt 14; and unit 28 receives, amplifies and processes the echo signal from the ultrasonic transducer to provide a measurement of bolt length or elongation. Examples of ultrasonic transducer units are shown, e.g., in U.S. Pat. Nos. 3,759,090, 3,810,385, 3,969,810 and 4,413,518 and 4,471,651, all of which are incorporated herein by reference.

The structure described above is, with the exception of modifications to the ultrasonic transducer unit 10 in accordance with this invention, generally known in the art. The transducer unit 10 is modified in accordance with this invention as more fully shown and described with respect to FIGS. 2–4. A vacuum line 30 extends from the interior of transducer unit 10 to a vacuum unit 32 such as a vacuum pump.

Figure 2:
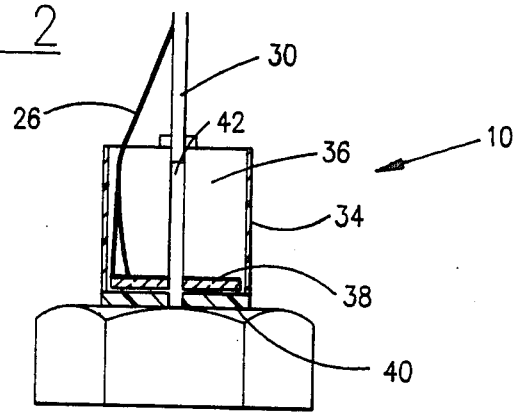
FIG. 2 is a partial sectional elevational view of the part of the transducer encircled in FIG. 1.
Figure 3:
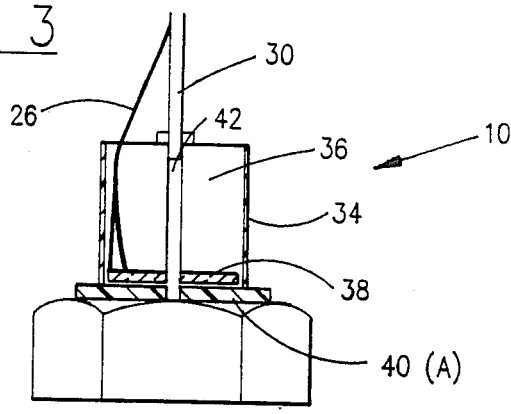
FIG. 3 is a view similar to FIG. 2 showing a modification.
Figure 4:
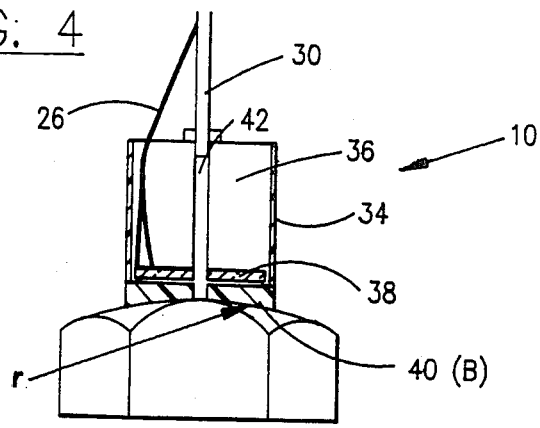
FIG. 4 is a view similar to FIG. 2 showing another modification.

Referring to FIGS. 2–4, the details are shown of the transducer 10 modified in accordance with the present invention. Referring first to FIG. 2, transducer 10 has an outer case 34 which houses transducer body or block 36. A piezoelectric crystal 38 is mounted in body 36, the electrical signal transmission line 26 is connected to crystal 38. A flexible and ultrasonically compatible end cap or seal element 40 is bonded to crystal 38 and block 36. Face or seal element 40 may be any suitable elastomeric sheet, preferably a cast urethane material.

A central passageway 42 extends through the entire length of transducer unit 10, including through block 36, crystal 38 and end cap or seal 40. Vacuum line 30 is attached by any suitable means to the end 31 (see FIG. 1) of the transducer unit 10 remote from the fastener, and passageway 42 forms, in effect, a continuation of vacuum line 30 to the outer surface of flexible end cap or seal 40.

In use, transducer unit 10 is mounted on the head end of the bolt to be measured, and a vacuum is pulled by vacuum unit 32. The force produced by the vacuum at the transducer/bolt interface pulls the transducer into firm engagement with the head to hold the transducer on the bolt head. An interface seal is established by flexible cap or seal 40 which conforms to the head of the bolt to form an air tight seal. Thus, firm and continuous contact is established between the transducer and the bolt to permit reliable ultrasonic extensometer measurements to take place.

In the embodiment of FIG. 2, the end cap or seal 40 is of the same size as the end of transducer unit 10 and is sized and configured to be compatible with small ground bolts. The embodiment of FIG. 3 differs from that of FIG. 2 only in that the end cap or seal 40(a) is larger than the end of transducer unit 10, the larger end seal of FIG. 3 being sized and configured for large bolts. The embodiment of FIG. 4 differs from that of FIGS. 2 and 3 only in that end cap 40(b) is configured with a radius "r" to make it compatible with small difficult bolts. Of course, it will be understood that other end cap configurations may be employed depending on particular requirements.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. Apparatus for attaching a transducer to a fastener element, the apparatus including:

housing means for containing a transducer;
transducer means within said housing means;
seal means at an end of said housing means intended to be mounted on a fastener element;
passage means through said housing means, said transducer means and said seal means; and
vacuum means connected to said passage means to pull a vacuum to bring the transducer into firm engagement with a fastener when mounted on the fastener.

2. The apparatus of claim 1 wherein:
said transducer means includes piezoelectric crystal means; and
said passage means extending through said piezoelectric crystal means.

3. The apparatus of claim 1 wherein:
said seal means includes elastomeric means mounted on one end of said housing means; and
said passage means extending through said elastomeric means.

4. The apparatus of claim 3 wherein:
said elastomeric means is sized or contoured to be compatible with a fastener on which it is to be mounted.

5. The apparatus of claim 3 including:
a contoured radiused external surface on said seal means.

* * * * *